(12) United States Patent
Nair et al.

(10) Patent No.: US 8,034,019 B2
(45) Date of Patent: Oct. 11, 2011

(54) DUAL MICROCONTROLLER-BASED LIQUID INFUSION SYSTEM

(75) Inventors: Bipin Nair, Kollam (IN); Krishnan Guruvayurappan, Coimbatore (IN); Harish Kumar, Kochi (IN)

(73) Assignee: Amrita Vishwa Vidyapeetham, Kollam (IN)

( * ) Notice: Subject to any disclaimer, the term of this patent is extended or adjusted under 35 U.S.C. 154(b) by 43 days.

(21) Appl. No.: 11/942,610

(22) Filed: Nov. 19, 2007

(65) Prior Publication Data

US 2008/0255517 A1 Oct. 16, 2008

(51) Int. Cl.
*A61M 31/00* (2006.01)
*A61M 37/00* (2006.01)

(52) U.S. Cl. .......................................... 604/67; 604/155

(58) Field of Classification Search .................. 604/30, 604/31, 65–67, 151, 152, 154, 155, 246, 604/503, 504, 890.1
See application file for complete search history.

(56) References Cited

U.S. PATENT DOCUMENTS

| | | | |
|---|---|---|---|
| 4,468,221 A | 8/1984 | Mayfield | |
| 4,498,843 A | 2/1985 | Schneider et al. | |
| 6,248,093 B1 | 6/2001 | Moberg | |
| 6,485,465 B2 * | 11/2002 | Moberg et al. | 604/154 |
| 6,656,148 B2 | 12/2003 | Das et al. | |
| 6,659,178 B2 | 12/2003 | Wilson et al. | |
| 6,742,992 B2 * | 6/2004 | Davis | 417/45 |
| 6,749,586 B2 | 6/2004 | Vasko | |
| 6,852,104 B2 | 2/2005 | Blomquist | |
| 2002/0077852 A1 * | 6/2002 | Ford et al. | 705/2 |
| 2003/0065308 A1 * | 4/2003 | Lebel et al. | 604/891.1 |
| 2003/0195462 A1 * | 10/2003 | Mann et al. | 604/67 |
| 2007/0210157 A1 * | 9/2007 | Miller | 235/435 |

* cited by examiner

*Primary Examiner* — Nicholas D Lucchesi
*Assistant Examiner* — Nathan R Price
(74) *Attorney, Agent, or Firm* — Law Office of Bommannan

(57) ABSTRACT

A highly reliable and robust functioning liquid infusion system for use in biomedical applications comprises a dual microcontroller system where the first microcontroller is configured to administer the liquid and the second microcontroller is configured to monitor the accurate functioning of the system and various performance parameters such as flow rate of liquid, presence of leaks or blocks in the liquid passage, level of drug in the cartridge and battery condition. The liquid injection portion comprises a cylindrical airtight liquid holder or drug cartridge with a movable internal piston that is in contact with a movable stem, and a micromotor, which controls the drug delivery. The system is programmable with a dosing system stored into the driver/monitor microcontrollers. A low power LCD module is used to display the operating parameters with multiple language interface and alarm conditions, if any. The system is also equipped with a system of sensors that trigger an alarm to indicate abnormal conditions.

16 Claims, 5 Drawing Sheets

DUAL MICROCONTROLLER-BASED LIQUID INFUSION SYSTEM

FIELD OF THE INVENTION

This invention relates generally to systems for liquid infusion into the body and specifically to liquid medication delivery systems, such as insulin pumps.

The following describes the invention, which is part of the research initiative of the TIFAC CORE in Biomedical Technology.

DESCRIPTION OF THE RELATED ART

Extensive research has consistently shown that tight control of blood glucose levels can prevent the onset and progression of diabetic complications. In a large majority of cases of diabetes, carefully regulated administration of insulin is essential to achieve good blood glucose control. Parenteral insulin injections have been in use for several decades. However, patients on injected insulin suffer from several drawbacks such as limitation on the number of times the drug can be delivered, the need to regulate their lifestyle in tune with the daily dose, time lag in action of the drug due to the need to use longer acting medications, etc. Insulin pumps greatly simplify the lifestyle of such patients by delivering in a programmed way continuous doses of small amounts of fast acting insulin as well as high 'bolus' doses to coincide with meal times in order to take care of the higher glycemic load.

Miniaturized infusion pumps have been developed for delivering liquid medicaments such as insulin to a patient. These infusion systems have the ability to offer sophisticated fluid delivery profiles accomplishing bolus requirements, continuous infusion and variable flow rate delivery. These infusion capabilities usually result in better efficacy of the drug and therapy and less toxicity to the patient's system. These pumps can deliver insulin on a continuous basal basis as well as a bolus basis as is disclosed in U.S. Pat. No. 4,498,843 to Schneider et al., for example.

The ambulatory pumps often work with a reservoir to contain the liquid medicine, such as a cartridge or syringe, and use electromechanical pumping or metering technology to deliver the medication to the patient via tubing from the infusion system to a needle that is inserted subcutaneously. The systems allow control and programming via electromechanical buttons or switches located on the housing of the system, and accessed by the patient or clinician. The systems include visual feedback via text or graphic screens, such as liquid crystal displays (LCDs), and may include alert or warning lights and audio or vibration signals and alarms. The system can be worn in a harness or pocket or strapped to the body of the patient.

Common problems with infusion pumps are leaks in the attached tubing, blockage of the fluid passage either in the tube or elsewhere, battery failure or in some cases, malfunction of the microprocessor. Many existing systems rely on the patient to visually inspect the system and monitor at least some aspects of its functioning such as liquid level in the drug cartridge, leaks in the tubing or connections and the quantum of fluid flow itself. However, monitoring would be difficult for patients with visual impairment or very young or disabled patients. There is therefore a need to provide a monitoring system within the device that measures a number of parameters such as dose administration, leakage or block in the tubing, battery condition, liquid level in the drug cartridge or other malfunction of the control microprocessor. Devices disclosed in U.S. Pat. No. 6,749,586 to Vasko provide for remote monitoring of the device, if necessary, on a continuous basis. Nevertheless, a self-contained device with an independent internal monitoring system has several advantages, at least one of them being fault diagnostics and display being directly available on the device.

Existing infusion pumps that use solenoid actuators have the drawback of high power consumption. For example, U.S. Pat. Nos. 4,468,221 and 6,248,093 describes such infusion pump. Other pumps are available with ultrasonic motors (for example, U.S. Pat. No. 6,659,178), which are expensive. Also, existing devices use microprocessors, such as those disclosed in U.S. Pat. No. 6,852,104 by Blomquist, which have high power consumption architecture. Whereas, the use of advanced power saving micro controllers, which are nanowatt, CMOS devices with built in CPU, clock, memory and user interfaces is likely to extend battery life through lower power consumption as well as lead to smaller size of the device.

Another problem in the prior art devices is sensing and generation of alarm signal due to occlusion in the fluid passage. For this purpose, U.S. Pat. No. 6,656,148 by Das et al., discloses pressure sensing using a force sensor, which has limitations of poor sensitivity and slow response.

Currently available insulin pumps have many shortcomings with their displays. They tend to use small screens, and hence small font sizes, as the devices generally have a small form factor. However, many people affected by diabetes also tend to have vision problems. Therefore, a large sized display will be advantageous. Another issue is that the display and operating instructions tend to be in English. A large percentage of the world's population exists in countries where English is not widely spoken or understood. Therefore, there is a need to have display capability in an additional language other than English. A particularly user-friendly feature is that the device should be safe against incursion of external water and other liquids into the device and also against internal leaks of the infusion liquid, which would damage or cause error in operation of the mechanism and electronics.

While the above description focuses on the problems associated with insulin pumps, it is well established that infusion pumps, in general, suffer from similar problems as described above.

There is therefore a need to develop a low cost infusion system that is energy efficient and has long battery life, is self-contained in terms of operation and monitoring, while at the same time enabling communication with external systems for programming or monitoring as the need may arise. Hence, an adaptively intelligent, automatic, low cost liquid delivery system for the administration of insulin and other such medications would be highly desirable.

SUMMARY OF THE INVENTION

The invention is a liquid infusion system for use in biomedical applications comprising a dual microcontroller system; a liquid infusion portion comprising a liquid holder, and a micromotor for propelling the liquid.

In a preferred embodiment, the liquid infusion system consists of a first and a second microcontroller system; where the first microcontroller is configured to administer the liquid and the second microcontroller is configured to monitor the accuracy of functioning of the system and various performance parameters such as flow rate of liquid, presence of leaks or blocks in the liquid passage, level of drug in the cartridge and battery condition. The liquid injection portion consists of a cylindrical airtight liquid holder or drug cartridge with a movable internal piston that can be placed securely in contact with a movable stem and a micromotor which in turn causes a precision screw to rotate by a pre-specified angular value in response to a stimulating signal to cause precise linear motion of the movable stem. Dosing is controlled through a system programmed into the driver/monitor microcontrollers wherein the program is stored in an electrical erasable programmable memory. A low power LCD module displays the operating parameters and separate batteries are provided to maintain the program memory and for driving the micromotor. A system of movement sensors transmits signal to both the driver and the monitor to indicate full, empty and liquid level conditions of the drug cartridge, and a current sensor coupled to the motor circuit is used to detect blockage of the fluid passage.

BRIEF DESCRIPTION OF THE DRAWINGS

The invention has other advantages and features that will be more readily apparent from the following detailed description of the invention and the appended claims, when taken in conjunction with the accompanying drawings, in which:

DETAILED DESCRIPTION OF THE PREFERRED EMBODIMENTS

Figure 1:
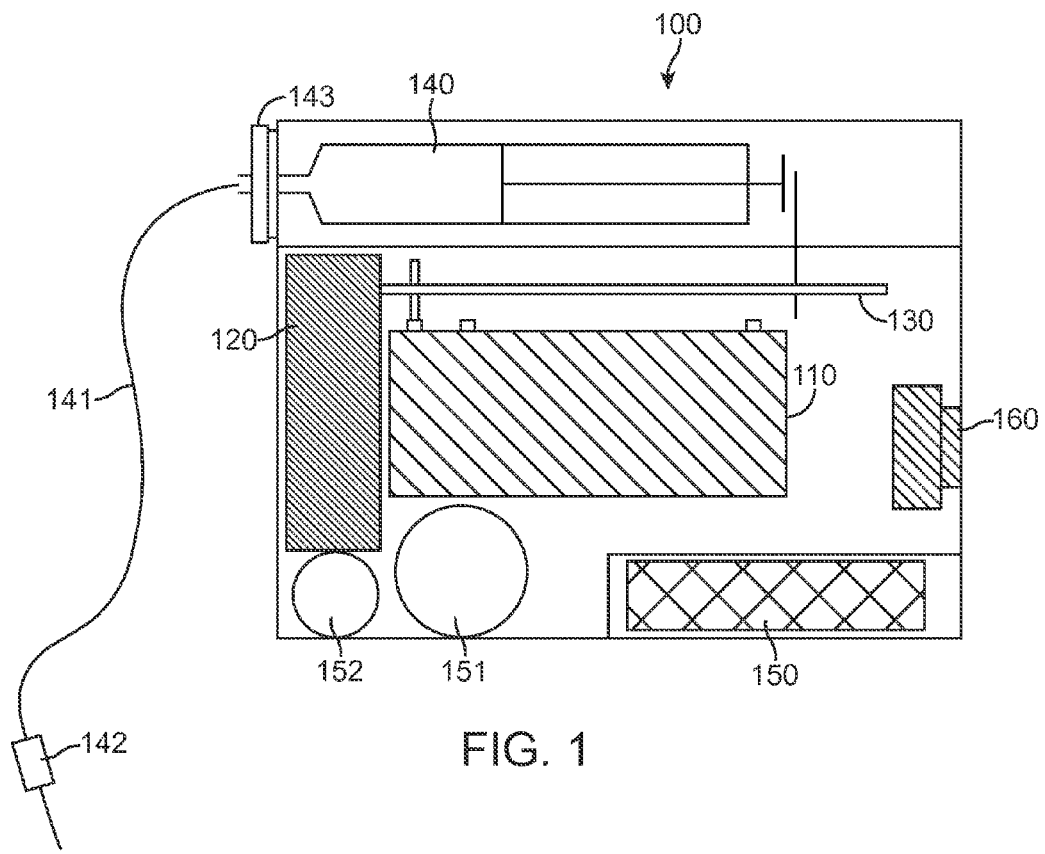
FIG. 1 is a schematic of the infusion system, showing the various components

The invention is a dual microcontroller-driven subcutaneous liquid infusion system for use in biomedical applications. The infusion system (sometimes referred to as micro-inserter) of the present invention is shown schematically in FIG. 1. The system 100 consists of a dual microcontroller assembly 110 that controls operation of a micromotor 120 to drive a precision screw 130. The microcontrollers are nanowatt, CMOS devices with built-in CPU, clock, memory and user interface. Rotation of precision screw 130 causes the airtight liquid container 140 to discharge the drug through flexible delivery tube 141 and injector 142. A removable threaded cap nut 143 facilitates snug fitting of the liquid holder directly into the micro-inserter. The micromotor is driven by the main battery 150, while the microcontroller assembly is energized by lithium battery 151. Alarm conditions are signaled by a buzzer 152 and the microcontrollers can be connected to an external data source such as a computer or other system through any number of compatible data exchange ports, particularly a USB interface 160.

Figure 2:
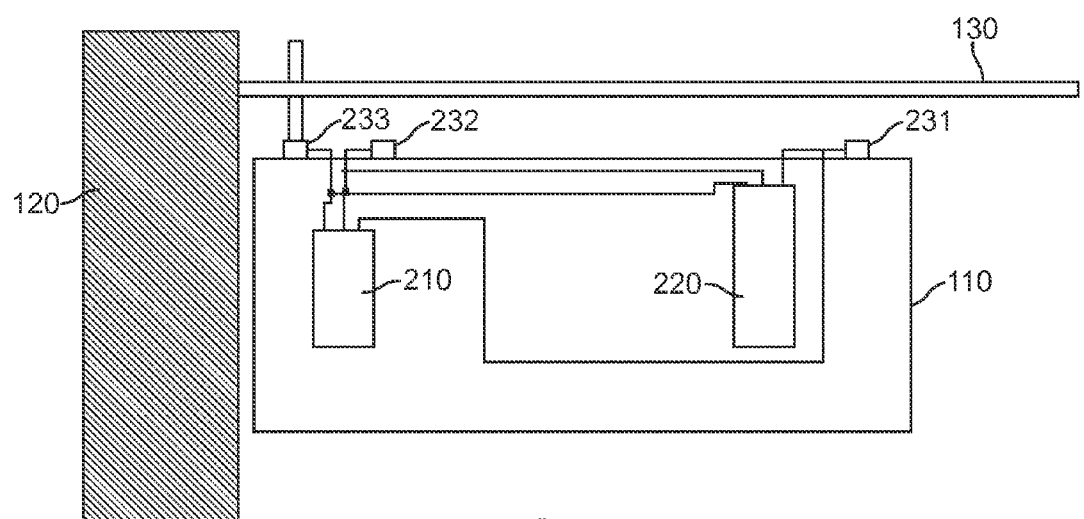
FIG. 2 shows the sensors and control system

One microcontroller of the micro-inserter orchestrates the liquid delivery and is henceforth referred to as the driver 210 (FIG. 2). The second microcontroller 220, henceforth called as monitor, continuously monitors the accuracy of the functions of the driver. The micro-inserter has three optical position sensors that define the start, stop and the movement in between of the injection piston. The start optical sensor 231 triggers the transmission of a signal simultaneously to both the driver and the monitor upon a well defined physical condition—when the drug cartridge is full. The stop optical sensor 232 triggers the transmission of a signal simultaneously to both the driver and the monitor upon the second well defined physical condition—when the drug cartridge is empty. The movement optical sensor 233 triggers the transmission of a signal simultaneously to both the driver and the monitor upon the third well defined physical condition—rotation of the precision screw 130. Automatic indication of the liquid level in the drug cartridge is thus achieved based on the data received from the sensors.

Figure 3:
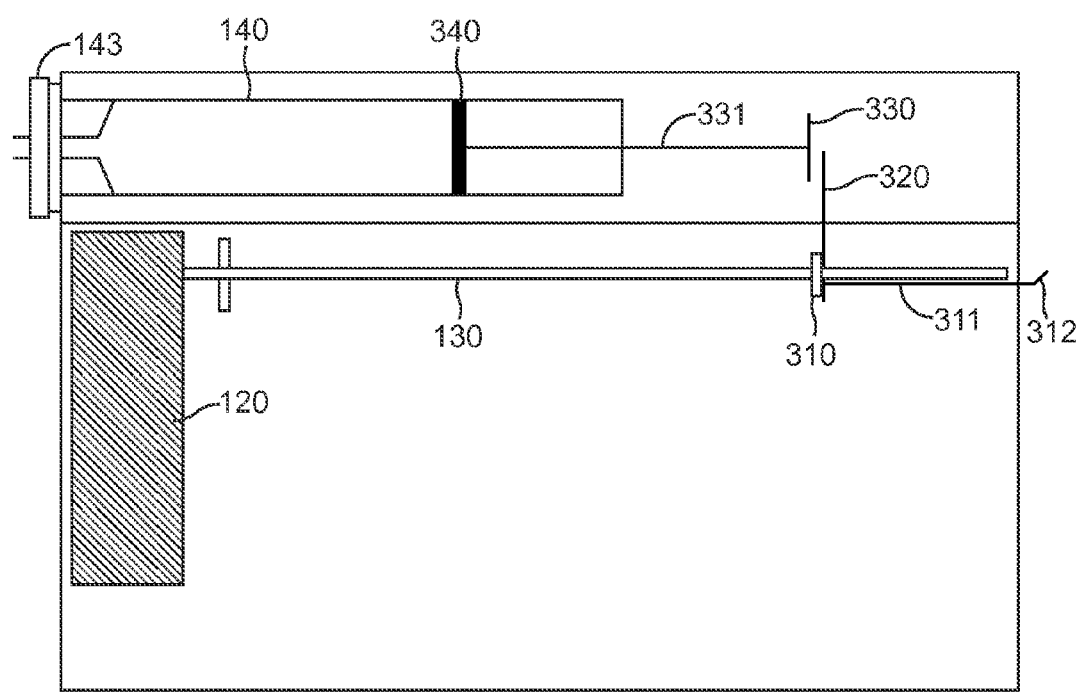
FIG. 3 shows the piston drive and disengagement mechanism

The drive mechanism for discharging the drug from the liquid holder is shown in FIG. 3. Movement of the precision screw 130 is transmitted to a precision nut 310 and vertical micro-lever 320, which pushes plunger 330, stem 331 and piston 340 against the drug cartridge fitted inside the cylinder 140. The precision nut can be caused to disengage from the precision screw 310, by a counter clockwise 30 degree manual rotation of a horizontal micro-lever 311 using a micro-knob 312 that protrudes outside the system. The rotation of the micromotor 120 is designed to be unidirectional, which prevents backward movement of the stem, thereby preventing negative pressure build-up and undesirable reverse inflow of fluids back into the liquid holder.

Figure 4:
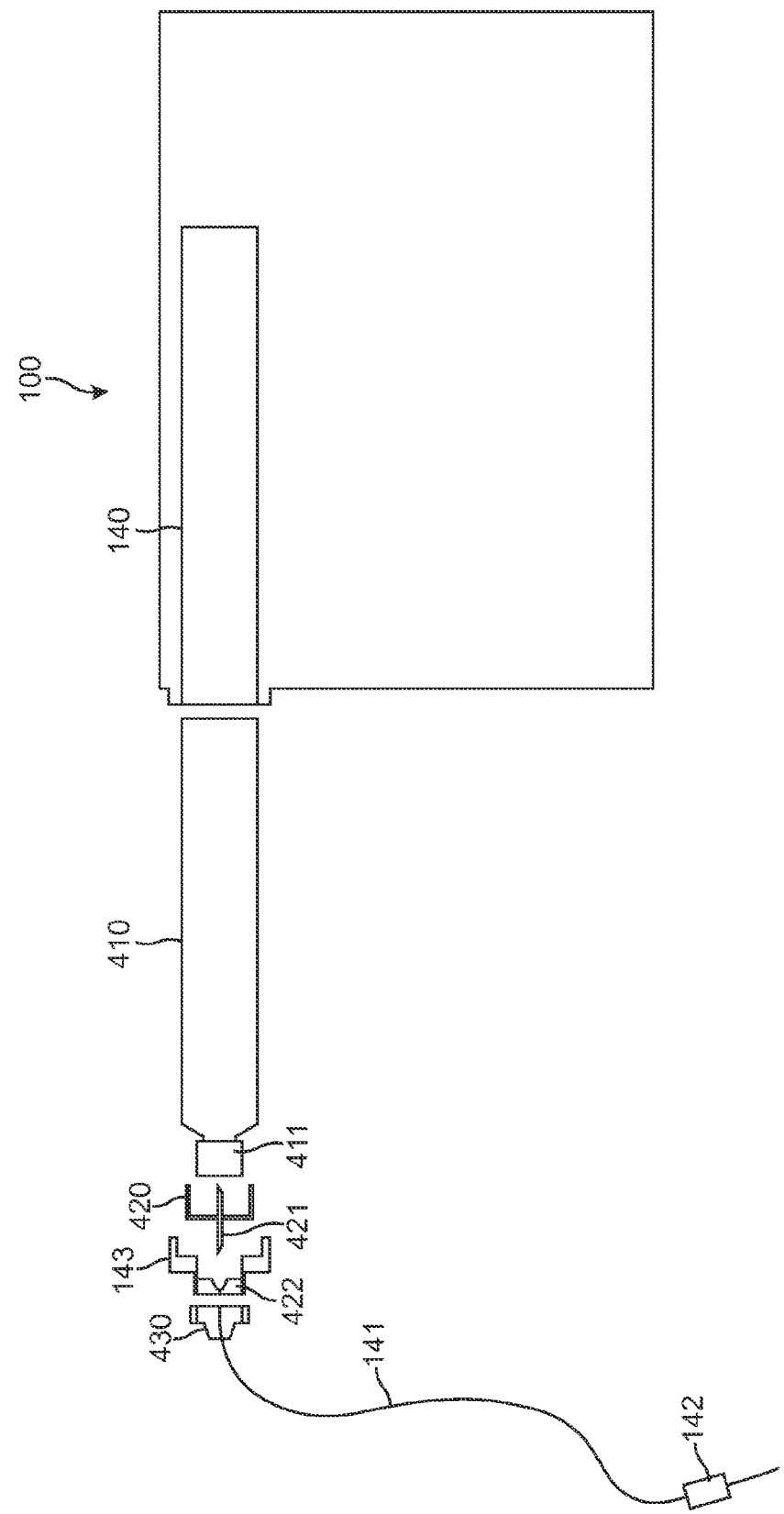
FIG. 4 shows the drug cartridge loading arrangement

The drug cartridge loading and delivery mechanism is shown in FIG. 4. The drug cartridge 410, fitted with needle cap 420, is inserted into the airtight cylinder 140 and turning the threaded cap nut 143 causes the needle 421 to pierce the cartridge cap 411 and the rubber separator or septum 422. The drug delivery tube 141 is connected to the threaded needle cap using a luer-lock fitting 430. To replace the drug cartridge when empty, referring to FIG. 3, the new cartridge is inserted into the cylinder 140 after disengaging the precision nut 310 from the precision screw 130 using the horizontal micro-lever 311. This automatically pushes the entire assembly comprising piston 340, vertical micro-lever 320 and precision nut 310 back to the starting position. Using the vertical micro-lever 320 to disengage the precision nut 310 from the precision screw enables movement of the precision nut to the starting point of the piston movement, which happens automatically when the new liquid cartridge is inserted into the holder. Reverse movement of the motor to move the nut is thus avoided, saving battery power.

Another aspect of the infusion system is its ability to withstand exposure to moisture and water. The single block casing, with one or more sealing O-rings, makes the system water-proof or at least water-resistant.

Figure 5:
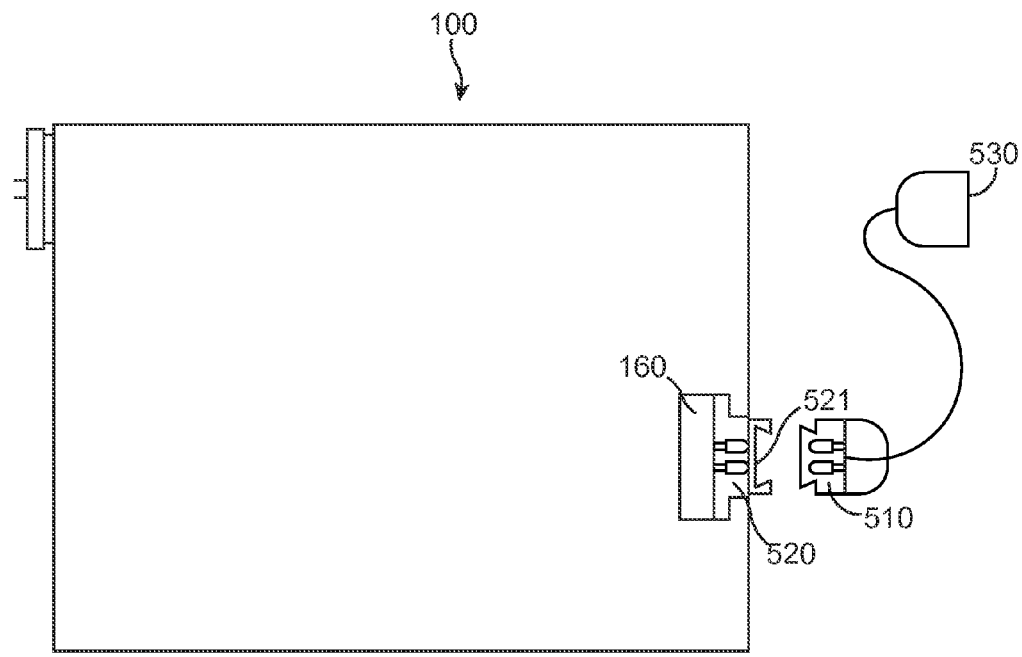
FIG. 5 shows the waterproof IR mode USB port connector for transfer of liquid delivery data to a PC
Figure 6:
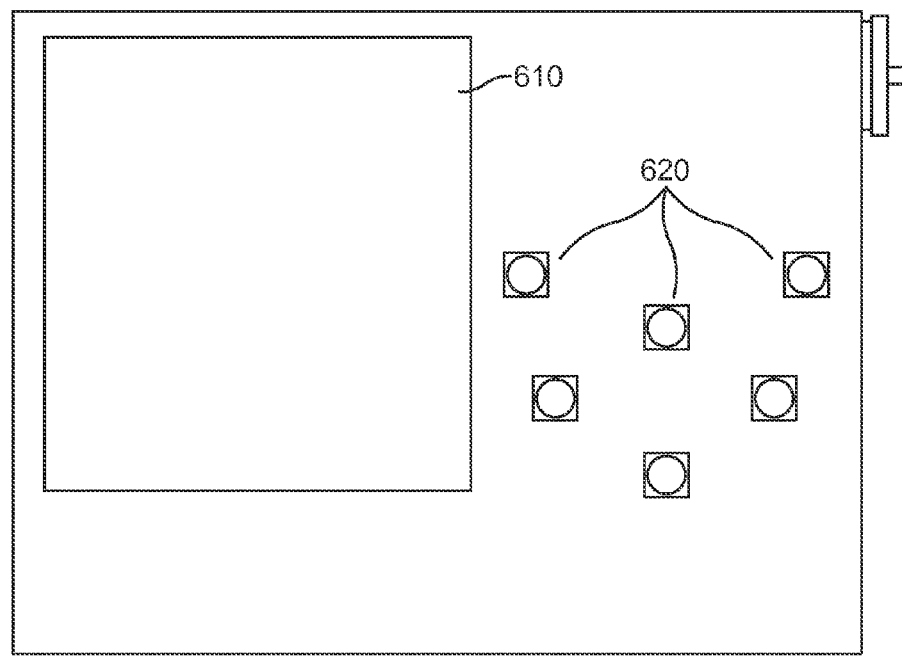
FIG. 6 is a drawing of large LCD module for data display with keys and input

The USB interface 160 (FIG. 5) achieves data transfer to/from the micro controller via signal conversion to optical/electrical through pairs of infrared transceiver ports, one external (510) and the other internal (520), with a transparent fluid proof screen 521 between them, rendering the USB port watertight. The detachable external IR port 510 extends to a standard USB interface connector 530 that can be connected to a PC or any other data exchange device. Data entry and readout are also facilitated by a large format LCD screen 610 (FIG. 6) and data entry keys 620 provided on the face of the device. Data entry could also be performed using a touch screen.

The dosing parameters are stored in an electrical erasable programmable memory (EPROM) and displayed through a low power LCD module. To inject a required quantity of the drug, the driver transmits a signal to a micromotor, which in turn causes a precision screw to rotate by a pre-specified angular value. A vertical micro-lever nut engaged with the precision screw causes the stem of the piston to move linearly by a pre-specified length in response to the pre-specified angular rotation of the precision screw. The pre-specified linear movement of the stem pushes the piston of the liquid holder resulting in pre-defined unit discharge of the liquid and the movement sensor transmits a signal to both the driver and the monitor. The dosing parameters could include a basal level infusion with the capability of a user-activated bolus infusion. The infusion device could, of course, be communicating with an external controller via wireless exchange. The external controller could be a cellular phone, PDA or other such systems. The external controller could be also be used to act as the intermediary between the patient and the doctor, where the dosing parameters for the particular patient could be remotely communicated by the doctor to the external controller, which in turn could communicate with the infusion system through the data exchange ports.

Figure 7:
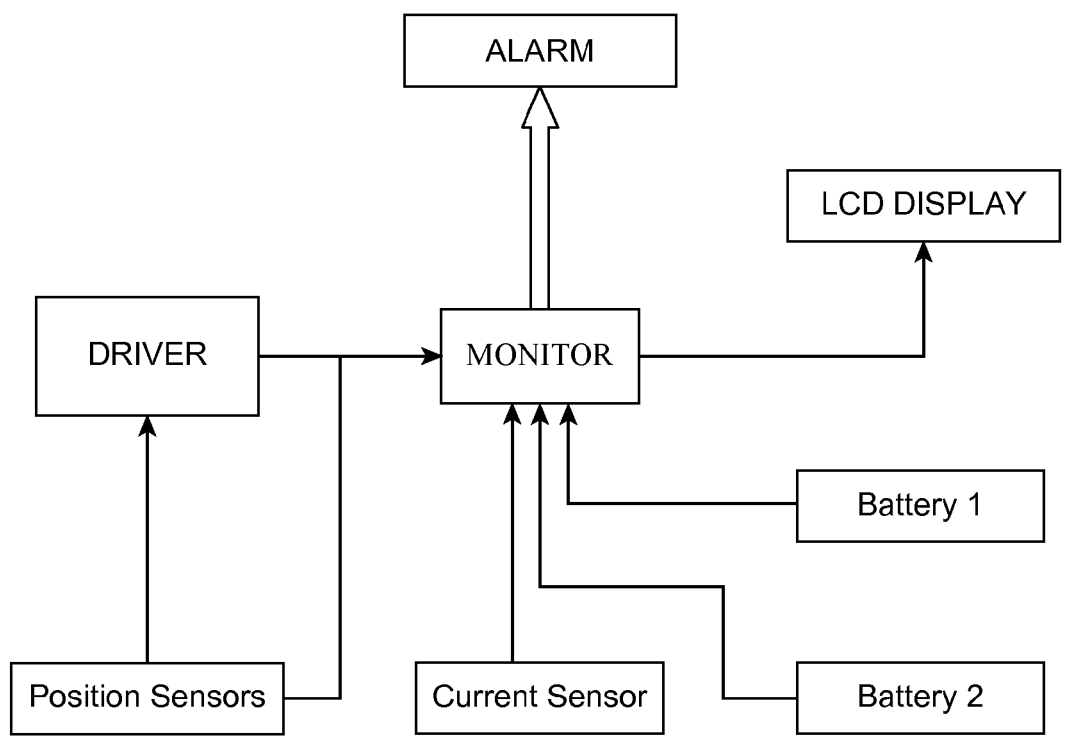
FIG. 7 is a schematic of the alarm annunciation logic

An important embodiment of the present invention is the dual microcontroller arrangement that enables independent monitoring of the functioning of the system and generate alarms when abnormal conditions are reached, as shown schematically in FIG. 7. The monitoring microcontroller receives inputs from the liquid level and motion sensors as to the start, stop and movement conditions of the injection piston 340 (shown in FIG. 3). The monitor also receives measurements of the drive current in the DC micromotor. An audible alarm and corresponding visual indication in the LCD screen are generated when pumping starts and when liquid in the cartridge is exhausted. During normal operation, liquid level is indicated by the LCD screen. Monitoring of the drive current in the DC micromotor is carried out by the microcontroller 220. During normal operation of the pump, the operating current of the DC motor is within a predetermined range. Aberrant operation due to leakage in the tube or the connections is indicated by reduced current while blockage of the tube is indicated by a higher than normal current. The microcontroller 220 signals an audible alarm and appropriate signal in the LCD display to indicate either of these two conditions and the user accordingly can take corrective action. Sensing of flow blockage by means of current sensing is instantaneous and accurate.

The monitor continually compares the driver's computational data output with pre-programmed values in its memory storage, any mismatch triggering an immediate halt of the driver, thereby causing stoppage of the stem movement and further liquid outflow. The halt signal results in an audible alarm. The software program to compute the dosing schedule can receive digital input directly from a sensor or a diagnostic system. The monitor also receives voltage signals from the drive battery 150 and the lithium battery 151, enabling it to perceive a change in the battery voltage characteristics indicating end of life or exhaustion of charge and give alarm and display signals appropriately. The dual microcontroller system thereby provides a high level of reliability and enables robust functioning of the system.

The programmable memory is capable of storing a plurality of schedules of dosing parameters, which are dynamically computed by a software program. The driver (microcontroller) reads the number of units by comparing the time of the day as per the stored schedule or computed schedule and transmits equal number of signals in succession to the micromotor. The stored schedules can be edited or altered using an interface such as a keyboard or a touchscreen. A multiple-language interface is provided for the LCD module, to enable interpretation. Scrolling of the cursor is not required given the large sized LCD module. The stored schedules can be edited either through the data entry keys, touch screen or altered by voice input on the system. Stored schedules or the software program itself can be transferred in and out of the micro controller via a plurality of data interfaces such as USB.

To change the liquid cartridge when it is empty, manual intervention is required to disengage the nut from the precision screw facilitating the free backward movement of the nut and its attached stem upon reloading of a new drug cartridge into the micro-inserter.

While the invention has been described with particular focus on insulin as the drug, it should be understood that any drug that could be delivered on a programmed or on-demand basis by the patient would be an appropriate drug choice to be delivered by the infusion system described here. The drugs could be painkillers such as codeine, morphine, Demerol, oxycontin, etc., drugs that are well known in the art to benefit from on-demand or programmed delivery to the patient.

While the invention has been disclosed with reference to certain embodiments, it will be understood by those skilled in the art that various changes may be made and equivalents may be substituted without departing from the scope of the invention. Particularly, the dual microcontroller concept could be applied to several systems for delivery of medications to the body such as intravenous fluid pumps and the like. In addition, many modifications may be made to adapt to a particular situation or material to the teachings of the invention without departing from its scope.

What is claimed is:

1. A liquid infusion system for use in biomedical applications comprising:
    a liquid infusion portion comprising a liquid holder configured to store a liquid;
    a micromotor for propelling the liquid through a delivery tube;
    a driver microcontroller comprising a first CPU, a first clock, and a first memory unit, wherein the driver microcontroller is configured to administer the liquid using the micromotor; and
    a monitor microcontroller comprising a second CPU, a second clock, and a second memory unit, wherein the monitor microcontroller is configured to compare a data output of the driver microcontroller to one or more values in the second memory unit and to halt the driver microcontroller when there is a mismatch between the data output and the one or more values, thereby providing independent monitoring of the driver microcontroller;
    wherein the monitor microcontroller is further configured to monitor a drive current that powers the micromotor, and to determine (a) when the drive current rises above a predetermined range and, upon such determination, to generate an audible alarm indicating blockage of the delivery tube, and (b) when the drive current falls below the predetermined range and, upon such determination, to generate an audible alarm indicating leakage in the delivery tube;
    wherein the driver microcontroller and the monitor microcontroller are enclosed within a single housing, and wherein the micromotor is powered by a first battery and the driver microcontroller and the monitor microcontroller are powered by a second battery.

2. The infusion system of claim 1, wherein the monitor microcontroller is further configured to monitor one or more performance parameters, wherein the performance parameters are flow rate of liquid, presence of leaks or blocks in the liquid passage, level of drug in a drug cartridge and the battery condition.

3. The infusion system of claim 1, wherein the liquid infusion portion comprises a drug cartridge chamber, a sealed piston arrangement, a stem leading from the piston to a plunger handle and a lever attached to a microscrew.

4. The infusion system of claim 3, wherein the sealed piston arrangement comprises a double O-ring system.

5. The system of claim 1 in which rotation of the micromotor is unidirectional.

6. The system of claim 1, further comprising a third programmable memory unit wherein the programmable memory unit stores a plurality of schedules of dosing parameters, which are dynamically computed by a software program.

7. The system of claim 2, wherein the liquid infusion system is configured to generate an audible alarm when there is a mismatch between the data output of the driver microcontroller and the one or more values that are stored in the second memory unit.

8. The system of claim 1, comprising an interface for data transfer.

9. The system of claim 8, where multilingual data display is available through a large format LCD screen.

10. The system of claim 8, where the data transfer is through an infrared USB connection.

11. The system of claim 8, where data is input through a data entry mechanism.

12. The system of claim 11, where the data entry mechanism is a voice activation mechanism.

13. The system of claim 3, wherein the micromotor is configured to move the stem by rotating a precision screw by a pre-specified angular value in response to a stimulating signal.

14. The system of claim 6 further comprising separate battery means to maintain the programmable memory unit and the micromotor.

15. The system of claim 1 further comprising a plurality of movement sensors configured to transmit a signal to the driver microcontroller and the monitor microcontroller to indicate a liquid level of the drug cartridge.

16. The system of claim 1 further comprising a current sensor coupled to a motor circuit to detect blockage of fluid passage.

* * * * *